United States Patent [19]

VanDeripe

[11] Patent Number: 5,204,085
[45] Date of Patent: Apr. 20, 1993

[54] METHOD FOR ENHANCING THE SAFETY OF METAL-LIGAND CHELATES AS X-RAY CONTRAST AGENTS

[75] Inventor: Donald R. VanDeripe, Lake St. Louis, Mo.

[73] Assignee: Mallinckrodt Medical, Inc., St. Louis, Mo.

[21] Appl. No.: 793,527

[22] Filed: Nov. 18, 1991

Related U.S. Application Data

[60] Division of Ser. No. 383,056, Jun. 22, 1989, Pat. No. 5,082,649, which is a continuation of Ser. No. 68,588, Jun. 30, 1987, abandoned, which is a continuation of Ser. No. 905,765, Sep. 9, 1986, abandoned, which is a continuation of Ser. No. 692,514, Jan. 8, 1985, abandoned.

[51] Int. Cl.$^5$ .................... A61K 49/04; A61K 31/28
[52] U.S. Cl. .......................................... 424/4; 424/9; 514/492; 514/836
[58] Field of Search ............... 424/4, 9; 514/836, 492

[56] References Cited

U.S. PATENT DOCUMENTS

| | | | |
|---|---|---|---|
| 4,176,173 | 11/1979 | Winchell et al. | 424/5 |
| 4,478,816 | 10/1984 | Ledley et al. | 424/4 |
| 4,647,447 | 3/1987 | Gries et al. | 424/9 |
| 4,810,782 | 3/1989 | Theodoropulos | 534/15 |
| 4,822,594 | 4/1989 | Gibby | 424/9 |
| 5,082,649 | 1/1992 | VanDeripe | 424/9 |

FOREIGN PATENT DOCUMENTS 736432 9/1955 United Kingdom .

*Primary Examiner*—Glennon H. Hollrah
*Assistant Examiner*—Gary E. Hollinden
*Attorney, Agent, or Firm*—Senniger, Powers, Leavitt & Roedel

[57] ABSTRACT

Paramagnetic chelates, as for example, Gadolinium diethylenetriaminepentaacetic acid (DTPA), manganese, ethylenediaminetetraacetic acid (EDTA), and others used as X-ray contrast agents are more toxic acutely when injected in high concentration or at rapid rates. The use of effective amounts of calcium in the form of, calcium chloride, calcium gluconate, or balanced salt solutions substantially reduces this toxicity without the need to add additional ligand.

13 Claims, No Drawings

METHOD FOR ENHANCING THE SAFETY OF METAL-LIGAND CHELATES AS X-RAY CONTRAST AGENTS

This is a division of application Ser. No. 07/383,056, filed Jun. 22, 1989, U.S. Pat. No. 5,082,649 which is a continuation of application Ser. No. 07/068,588 filed Jun. 30, 1987, now abandoned which is a continuation of application Ser. No. 06/905,765 filed Sep. 9, 1986, now abandoned which is a continuation of application Ser. No. 06/692,514 filed Jan. 18, 1985 now abandoned.

BACKGROUND OF THE INVENTION

This invention relates to magnetic resonance imaging complexes and more particularly to methods for reducing the toxicity thereof.

It has been found that physiologically well-tolerated complex salts formed from the anion of a complexing acid (ligand) and one or more central ions of an element with an atomic number of 21 to 29, 42, 44 or 57 to 83 (paramagnetic metal) and, optionally, also formed from one or more Physiologically biocompatible cations of an inorganic and/or organic base or amino acid, are suitable for producing diagnostic media for use in magnetic resonance imaging or X-ray diagnosis. We have referred to these materials as paramagnetic metal chelates. U.S. Pat. No. 4,647,447 describes the use and the manufacture of paramagnetic metal chelates in detail.

However, it has been found that these paramagnetic chelates employed in magnetic resonance imaging acutely reflect more toxicity when injected in high concentration or at rapid rates. Generally, this toxicity has been manifested as strong convulsions.

Believing this toxicity to stem from the absorption of free paramagnetic metals in the blood, it has been the previous practice to reduce such toxicity by formulating with an additive of excess ligand such as EDTA as its sodium and/or calcium salts. These additives were employed as scavengers for the paramagnetic metal in the manner disclosed by Bernard Osler et al. in *Toxicology and Applied Pharmacology. Volume 5*. Pages 142-162 published in 1963 under title of "Safety Evaluation Studies of Calcium EDTA".

However, a method for reducing such toxicity without the need for employing excess ligand and without having to correlate the amount of excess ligand to the projected amount of free metal in the blood would be a substantial advancement in the art.

SUMMARY OF THE INVENTION

It is an object of this invention to provide enhanced safety in magnetic resonance imaging (MRI) by reducing the toxicity of paramagnetic chelate formulations.

It is a further object of this invention to provide enhanced safety in X-ray contrast imaging by reducing the toxicity of heavy metal chelates.

Upon further study of the specification and appended claims, further objects and advantages of this invention will become apparent to those skilled in the art.

It has been found that adding calcium ions in substantially less than stoichiometric proportions to the metal-ligand chelates used in MRI or X-ray contrast formulation will substantially reduce the acute intravenous toxicity thereof.

DESCRIPTION OF THE PREFERRED EMBODIMENTS

In accordance with the present invention, calcium in the form of calcium gluconate, calcium chloride or other suitable organic or inorganic salts and including suitable soluble calcium forms of the chelant/ligand used to complex paramagnetic and/or heavy metals are added to the product formulation to be used for MRI or X-ray contrast imaging.

The calcium ions are added at levels ranging from 1-25% of stoichiometry based on the chelant/ligand concentration, but preferably from 3% to about 15% of stoichiometry.

The amount of calcium added is determined individually for each formulation and will depend on the calcium chelation potential of the formulation. The calcium can be added in a single form, e.g. calcium chloride, or as mixtures, e.g. calcium chloride and calcium gluconate.

The paramagnetic and/or heavy metal chelates to which calcium is to be added are complex salts formed from the anion of a complexing acid and a central ion of an element with an atomic number of 21 to 29, 42,44 or 57 through 83 and, optionally, also formed from one or more physiologically bio-compatible salts of inorganic and/or organic bases or amino acids. They are suitable for producing diagnostic media which are useful in magnetic resonance imaging and/or X-ray diagnosis. If the medium is intended to be used in magnetic resonance imaging, the central ion must be paramagnetic. It preferably is the divalent or trivalent ion of elements with an atomic number of 21 to 29, 42, 44 and 57 through 70. Suitable ions for example, chromium 3, manganese 2, iron 3, iron 2, cobalt 2, copper 2, praseodymium 3, neodymium 3, samarium 3, ytterbium 3 and because of their very strong magnetic moments gadolinium 3, terbium 3, dysprosium 3, holmium 3, and erbium 3 are preferred.

If the medium is intended for use in X-ray diagnosis, the central ion should be derived from an element with a higher atomic number to achieve a sufficient absorption of X-rays. It has been found that diagnostic media containing a physiologically well-tolerated complex salt with central ions of elements with atomic numbers of 57 to 83 are suitable for this purpose. These include, for example, lanthanum 3, the above-mentioned ions of the lanthanide group, gold 3, lead 2 and bismuth 3.

The action of citric acid, ethylenediaminetetraacetic acid (EDTA) and similar ligands to complex with ionic calcium when injected in vivo into the bloodstream and inducing tetanic convulsions has long been appreciated. Calcium administered as a chloride salt or as calcium gluconate is know to be effective in counteracting these convulsions. However, such teachings have previously found little application in reducing the toxicity of magnetic resonance agents or X-ray contrast agents. Among the prior art reasons for not resorting to ionic calcium in such applications may have been that ionic calcium if added at stoichiometric amounts would have been detrimental because these hypertonic solutions would then have provided excessive amounts of calcium upon injection into the bloodstream. Additionally, calcium complexation by iodinated X-ray contrast media was not significant compared to the newer paramagnetic complexes.

Complex paramagnetic chelates and heavy metals complexed to chelant ligands as previously stated have limited clinical utility at increasing dosages because of the toxicity created therefrom. Toxicity which is usually greater when the agents are injected rapidly and/or at more concentrated levels is generally attributed to the in vivo release of the heavy metal. Therefore, the addition of excess ligand to the formulation to bind any "free" metal in the injectable is felt to be of value. However, the effective scavenging amount of excess ligand at, for example, 15% excess sodium salt fails to enhance the safety of the $Na_2GdDTPA$. Addition of 15% excess ligand as the $CaNa_3DTPA$ to $Na_2GdDTPA$ increased the intravenous $LD_{50}$ about 20%. Although this level of excess ligand would provide about 4 mg/ml of calcium, the following examples show that further enhancement of safety can be expected by adjusting the level of calcium simply by addition of calcium chloride, i.e. without need for excess ligand.

The toxicity of the preferred embodiments of the present invention are measured by lethal dose (LD) values which are approximations of the doses at which the specimen animals die. Exemplary lethal does values for the present invention are seen in the examples set forth below:

EXAMPLE 1

The intravenous $LD_{50}$ for calcium chloride ($CaCl_2$) in the mouse is reported to be 42 mg/kg (RTECS). This calculates to about 15 mg/kg of calcium or about 0.3 mg of calcium for a 20 gram mouse. When calcium chloride was added to 0.68M disodium gadolinium diethylenetriaminepentaacetic acid ($Na_2GdDTPA$) at 130 mg/kg (6.5 mg/ml) or 260 mg/kg (13.0 mg/ml) the lethal effects of the $Na_2GdDTPA$ were greatly diminished even though these levels of added calcium would provide 47 and 94 mg/kg, i.e. 0.94 and 1.88 mg respectively to a 20 gram mouse. These values are 3.1 and 6.2 times higher than the i.v. $LD_{50}$ of calcium administered as $CaCl_2$. Whereas 4 of 4 mice given 13.6 mMol/kg of $Na_2GdDTPA$ died, only 1 of 4 mice died at those doses of $Na_2GdDTPA$ alone with 2.34 mg/ml of added calcium and 2 of 4 died at the 4.68 mg/ml level of added calcium. Clearly then the 0.68M $Na_2GdDTPA$ solution must complex a substantial amount of the added calcium in a way to block the calcium's in vivo toxicity.

Conversely, the calcium added to the $Na_2GdDTPA$ formulation blocks the in vivo calcium complexation by $Na_2GdDTPA$ and thereby reduces its toxicity, i.e. prevents tetanic convulsions and death. Clearly this protective effect of added calcium must be balanced to the calcium complexing potential of the paramagnetic contrast agent.

EXAMPLE 2

Addition of calcium chloride at 430 (21.5 mg/ml) and 860 mg/kg (43 mg/ml), i.e. at 155 and 310 mg of calcium/kg, results in doses of 3.1 and 6.2 mg of calcium per 20 gram mouse. These doses of calcium added to 0.68M $Na_2GdDTPA$ were not protective and did not enhance the safety of the $Na_2GdDTPA$ formulation. All mice injected with 0.65M $Na_2GdDTPA$ at those two dose levels of calcium died. It may be inferred that these levels of added calcium were excessive and exceeded the calcium binding optimum of the solution and that death from calcium toxicity ensued.

In these examples 1 and 2 (see Table 1) it is shown that calcium added to 0.68M $Na_2GdDTPA$ as calcium chloride at concentrations of 6.5, 13.0, 21,5 and 43 mg/ml of solution and which would result in concentrations of calcium of 2.34 mg., 4.68 mg, 7.74 mg and 15.48 mg per milliliter respectively, provided different levels of protection against the toxicity of $Na_2GdDTPA$. On a stoichiometric basis the four added calcium levels approximate 9%, 17%, 29% and 57% respectively of the 0.68M concentration of $Na_2GdDTPA$. Based on this data, concentrations of added calcium of 30–60% stoichiometric to that of the subject formulation are excessive and do not enhance the safety. However, concentrations of added calcium of 9–17% stoichiometry to the subject formulations were protective based on acute toxicity determinations.

Clearly the optimum amount of calcium to be added will vary based on the ligand chosen and its concentration in the formulation.

TABLE 1

STUDIES OF INTRAVENOUS TOXICITY OF $Na_2GdDTPA$ ALONE AND ADDED $CaCL_2$

| Dose of $Na_2GdDTPA$ | Added Calcium mg/ml | Mice No. Deaths/ No. Injected | Approximate LD Values | Calcium, % Stoichiometry $Na_2GdDTPA$ |
|---|---|---|---|---|
| 13.6 mMol/kg | 0 | 4/4 | 100% | 0 |
| 13.6 mMol/kg | 2.34 | 1/4 | 25% | 9% |
| 13.6 mMol/kg | 4.68 | 2/4 | 50% | 17% |
| 13.6 mMol/kg | 7.74 | 4/4 | 100% | 29% |
| 13.6 mMol/kg | 15.48 | 2/2 | 100% | 57% |

What is claimed is:

1. In a method for enhancing safety in the in vivo use of metal-ligand chelate complexes as X-ray contrast agents comprising administering to a mammal a diagnostically effective amount of a metal-ligand complex, the improvement comprising:

adding calcium ions to a charge-balanced metal-ligand complex formed from the anion of a complexing acid and a central ion of an element with an atomic number of 57 to 83, said calcium ions being added in substantially less than stoichiometric amounted to the metal-ligand complex, said calcium ions being provided from a member of the group consisting of inorganic calcium salts, organic calcium salts and mixtures thereof without excess ligand being added.

2. The method of claim 1 wherein the metal-ligand chelate complex is used in the form of a salt.

3. The method of claim 1 wherein the metal-ligand chelate complex is used in non-ionic form.

4. The method of claim 1 wherein the calcium ions are provided at levels of from about 1 to about 25% of the stoichiometric amount required by the metal-ligand complex.

5. The method of claim 4 wherein the calcium ions are provided at levels of about 3 to about 15% of the stoichiometric amount.

6. The method of claim 1 wherein the calcium ions are provided in the form of calcium chloride.

7. The method of claim 2 wherein the calcium ions are provided at levels of from about 1 to about 25% of the stoichiometric amount required by the metal-ligand complex.

8. The method of claim 3 wherein the calcium ions are provided at levels of from about 1 to about 25% of the stoichiometric amount required by the metal-ligand complex.

9. The method of claim 7 wherein the calcium ions are provided at levels of about 3 to about 15% of the stoichiometric amount.

10. The method of claim 8 wherein the calcium ions are provided at levels of about 3 to about 15% of the stoichiometric amount.

11. In a method for enhancing safety in the in vivo use of metal-ligand chelate complexes as X-ray contrast agents comprising administering to a mammal a diagnostically effective amount of a metal-ligand complex, the improvement comprising: adding calcium ions to a charge-balanced metal-ligand complex formed from the anion of a complexing acid and a central ion of an element with an atomic number of 57 to 83, said calcium ions being added in substantially less than stoichiometric amounts to the metal-ligand complex, said calcium ions being provided from a member of the group consisting of inorganic calcium salts, organic calcium salts and mixtures thereof and being added to any calcium present as the salt of an excess of said ligand.

12. The method of claim 11 wherein the metal-ligand complex is used in the form of a salt.

13. The method of claim 11 wherein the metal-ligand complex is used in non-ionic form.

* * * * *